United States Patent [19]

Natarajan et al.

[11] 4,377,701
[45] Mar. 22, 1983

[54] 4-METHYLENE-1-[[(ALRANOYL OR ARYLCARBONYL)MERCAPTO]ACYL]PROLINE AND PIPECOLIC ACID

[75] Inventors: Sesha I. Natarajan, Neshanic Station; Miguel A. Ondetti, Princeton, both of N.J.

[73] Assignee: E. R. Squibb & Sons, Inc., Princeton, N.J.

[21] Appl. No.: 304,148

[22] Filed: Sep. 21, 1981

[51] Int. Cl.³ .................. C07D 207/22; C07D 211/78
[52] U.S. Cl. .................................... 548/533; 424/267; 424/274; 546/226; 546/245
[58] Field of Search .................. 260/326.43, 326.46; 546/226, 245

[56] References Cited

U.S. PATENT DOCUMENTS 4,105,776  8/1979  Ondetti et al. .................. 424/274
4,296,113  10/1981  Ondetti .......................... 424/246

OTHER PUBLICATIONS

Bethell et al., *J. Chem. Soc.*, 3850 (1965).
Jolles et al., *Bull. Soc. Chem.*, 1965 (8), pp. 2253–2259.

*Primary Examiner*—Richard Raymond
*Attorney, Agent, or Firm*—Lawrence S. Levinson; Donald J. Barrack

[57] ABSTRACT

Compounds having the formula

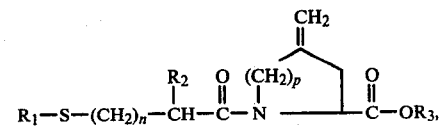

and salts thereof, wherein $R_1$ is a readily hydrolyzable acyl protecting group;
$R_2$ is hydrogen or alkyl;
$R_3$ is hydrogen, alkyl or arylalkyl;
n is 1 or 2; and
p is 1 or 2
inhibit the action of angiotensin converting enzyme.

9 Claims, No Drawings

4-METHYLENE-1-[[(ALRANOYL OR ARYLCARBONYL)MERCAPTO]ACYL]PROLINE AND PIPECOLIC ACID

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776, issued Aug. 8, 1979 discloses mercaptoacyl amino acids wherein the amino acid is, inter alia, proline, 4-hydroxyproline and 4-alkylproline.

BRIEF DESCRIPTION OF THE INVENTION

Compounds having the formula

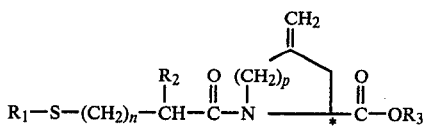

and salts thereof, inhibit the action of angiotensin converting enzyme, and are, therefore, useful for the treatment of hypertension. In formula I, and throughout the specification, the symbols are as defined below.

$R_1$ is a readily hydrolyzable acyl protecting group such as alkanoyl or arylcarbonyl;
$R_2$ is hydrogen or alkyl;
$R_3$ is hydrogen, alkyl or arylalkyl;
$n$ is 1 or 2; and
$p$ is 1 or 2.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are the preferred aryl groups; phenyl is the most preferred group.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having 2 to 9 carbon atoms.

The asterisk in formula I indicates a center of asymmetry in the ring. In the instance wherein the ring is proline (p is 1) this asymmetric center is in the L-configuration. In the instance wherein the ring is pipecolic acid (p is 2) this asymmetric center is in the D,L or L-configuration.

Depending on the definition of $R_2$, the sulfur containing sidechain may also contain an asymmetric center. The product of formula I, therefore, exists in stereoisomeric forms and as racemic or diastereomeric mixtures thereof. All are within the scope of this invention. The synthesis described below can utilize the racemate or one of the enantiomers as starting materials. When the racemic starting material is used, the stereoisomers obtained in the final product can be separated by conventional chromatographic or fractional crystallization methods. Preferably, if there is an asymmetric center in the sulfur containing side-chain, it is in the D-configuration.

DETAILED DESCRIPTION OF THE INVENTION

The compounds of formula I, and salts thereof, are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 300 to 300 mg. of a compound of this invention, and about 15 to 300 mg., preferably about 15 to 200 mg. of the diuretic, to a mammalian species in need thereof. Examplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared by reacting a 4-methylene substituted proline or pipecolic acid derivative having the formula

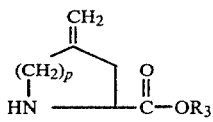

with an acyl halide having the formula

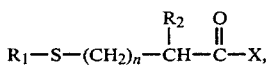

wherein X is a halogen, preferably chlorine. The reaction is preferably run in a two phase solvent system such as water/ether or water/ethyl acetate, in the presence of a base such as an alkali metal hydroxide or alkali metal carbonate.

The proline and pipecolic acid derivatives of formula II can be prepared from the corresponding amino acids having a protected nitrogen atom, preferably a benzyloxycarbonylamino protecting group. Treatment of the protected compound with an organic acid such as methanesulfonic acid yields the desired amino acid.

The compound of formula I wherein $R_3$ is hydrogen form basic salts (with various inorganic and organic bases) which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic physiologically acceptable salts are preferred, although other salts are also useful, e.g., in isolating or purifying the product.

The salts are formed in a conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Those products of formula I wherein n is 1, p is 1, and $R_2$ is methyl are preferred. Also preferred are those compounds of formula I wherein $R_3$ is hydrogen.

The following examples are specific embodiments of this invention.

EXAMPLE 1

(S)-1-[3-(Acetylthio)-2-methyl-1-oxopropyl]-4-methylene-L-proline

Benzyloxycarbonyl-4-methylene-L-proline (4.5 g; J. Chem. Soc., 3850 (1965)) is dissolved in methylene chloride (10 ml). Methanesulfonic acid (12 ml) and anisole (2.5 ml) are added, and the solution is evaporated to remove methylene chloride. The reaction mixture is kept at room temperature for forty-five minutes, and ether is then added to the reaction mixture; an oil is deposited at the bottom. Ether solubles are evaporated, dissolved in water and applied on an ion-exchange (H+) column (75 ml bed volume). Then the ether insoluble oil is dissolved in water and applied on the same column. The column is thoroughly washed with water until the washings are neutral. Then the column is washed with 1 N ammonium hydroxide until the compound fully emerges out. Ammonium hydroxide eluates are combined, evaporated and re-evaporated from absolute ethanol (yield 2.5 g), (thin-layer chromatography) $R_f=0.29$ (silica gel), n-butanol:acetic acid:water—4:1:1). The carbon NMR corroborates the structure of the amino acid to be the desired exomethyleneproline (173.69; 139.79; 110.17; 61.27; 48.89; 34.19 ppm).

4-Methyleneproline (2.3 g) is dissolved in aqueous sodium carbonate (2 N, 9 ml) and the solution is cooled in an ice-bath. D-3-(Acetylthio)-2-methylpropionyl chloride (7.25 g) in ether (5 ml) is added to the aqueous solution and the solution is stirred vigorously. The pH of the solution is maintained at 8.5 by the addition of sodium carbonate solution (4 N, 10 ml). After stirring the solution for ninety minutes it is extracted with ether (discarded). The aqueous solution is acidified to pH 2.0, extracted with ethyl acetate and concentrated (3.5 g). This is chromatographed on silica gel (150 g, Baker, mesh 60–200) using the solvent system benzene:acetic acid (10:2). Twenty milliliter fractions are collected and fractions 26–45 contain 3.1 g of the desired material.

A dicyclohexylamine salt is prepared of 3.0 g of product in ethyl acetate (30 ml) using dicyclohexylamine (2.4 ml). Yield 3.8 g $[\alpha]_D-60°$. The rotation is the same after recrystallization using acetonitrile as the solvent.

Anal. Calc'd. for $C_{24}H_{20}N_2SO_4$(DCHA Salt): C, 63.68; H, 8.91; N, 6.19; S, 7.08. Found: C, 63.40; H, 9.18; N, 5.98; S, 6.87.

EXAMPLE 2

(S)-1-[3-(Acetylthio)-2-methyl-1-oxopropyl]-4-methylene-L-pipecolic acid (A) Benzyloxycarbonyl-4-methylene-L-pipecolic acid To freshly condensed ammonia (170 ml) is added sodium (1.29 g) and a trace of ferric chloride. When the blue color has disappeared, methyltriphenylphosphonium bromide (20 g) is added with stirring. After removing ammonia, ether (75 ml) and tetrahydrofuran (75 ml) are added. The reaction mixture is heated for 5 minutes at 50° C. After cooling to room temperature, benzyloxycarbonyl-4-keto-L-pipecolic acid (2.77 g; Bull. Soc. Chem., 1965 (8) p. 2253–2259) dissolved in tetrahydrofuran (20 ml) is added over a period of ten minutes with stirring. The reaction mixture is refluxed overnight, and cooled and diluted with ether. The precipitated material is further purified by twice repeating the extraction procedure with aqueous sodium bicarbonate, acidification and extraction with ether.

(B) (S)-1-[3-(Acetylthio)-2-methyl-1-oxopropyl]-4-methylene-L-pipecolic acid

Following the procedure of example 1, but substituting benzyloxycarbonyl-4-methylene-L-pipecolic acid for benzyloxycarbonyl-4-methylene-L-proline, yields the title compound.

What is claimed is:

1. A compound having the formula

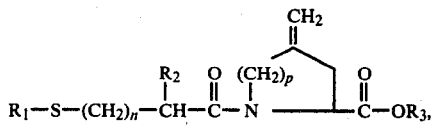

and salts thereof, wherein $R_1$ is alkanoyl or arylcarbonyl;

$R_2$ is hydrogen or alkyl;

$R_3$ is hydrogen, alkyl or arylalkyl;

n is 1 or 2; and p is 1 or 2.

2. A compound in accordance with claim 1 wherein $R_2$ is hydrogen.

3. A compound in accordance with claim 1 wherein $R_2$ is alkyl.

4. A compound in accordance with claim 3 wherein $R_2$ is methyl.

5. A compound in accordance with claim 1 wherein n is 1.

6. A compound in accordance with claim 5 wherein p is 1.

7. A compound in accordance with claim 5 wherein p is 2.

8. A compound in accordance with claim 1 wherein $R_3$ is hydrogen.

9. The compound in accordance with claim 1 (S)-1-[3-(acetylthio)-2-methyl-1-oxopropyl]-4-methylene-L-proline.

* * * * *

UNITED STATES PATENT AND TRADEMARK OFFICE
CERTIFICATE OF CORRECTION

PATENT NO. : 4,377,701
DATED : March 22, 1983
INVENTOR(S) : Sesha I. Natarajan, et al.

It is certified that error appears in the above—identified patent and that said Letters Patent is hereby corrected as shown below:

In the title, line 1, "ALRANOYL" should read --ALKANOYL--.
Column 1, line 1, "ALRANOYL" should read --ALKANOYL--.
Column 2, line 46, "300 to 300 mg." should read --30 to 300 mg.--
Column 2, line 49, "Examplary" should read --Exemplary--.

Signed and Sealed this

Seventeenth Day of May 1983

[SEAL]

Attest:

DONALD J. QUIGG

Attesting Officer   Acting Commissioner of Patents and Trademarks